United States Patent [19]

Goulter et al.

[11] Patent Number: 5,009,649

[45] Date of Patent: Apr. 23, 1991

[54] EXPANDABLE BANDED MALE URINARY INCONTINENCE CONDOM AND SUPPORTING UNDERGARMENT

[76] Inventors: Victor Goulter; Barbara Goulter, both of 485 Molimo Dr., San Francisco, Calif. 94127

[21] Appl. No.: 379,105

[22] Filed: Jul. 13, 1989

[51] Int. Cl.⁵ .............................................. A61F 5/44
[52] U.S. Cl. .................................... 604/351; 604/349
[58] Field of Search ................... 251/342; 2/400, 402, 2/403, 405; 604/349-353, 323, 335; 128/760, 842, 844; 222/518

[56] References Cited

U.S. PATENT DOCUMENTS

| 749,382 | 1/1904 | Henderson | 604/350 |
|---|---|---|---|
| 3,087,656 | 4/1963 | Dougherty | 222/518 |
| 3,520,305 | 7/1970 | Davis | 604/349 |
| 3,547,123 | 12/1970 | Sachs | 604/350 |
| 3,835,857 | 9/1974 | Rogers et al. | 604/349 |

FOREIGN PATENT DOCUMENTS

| 318242 | 1/1920 | Fed. Rep. of Germany | 604/350 |
|---|---|---|---|
| 1508356 | 1/1968 | France | 604/351 |
| 2094632 | 9/1982 | United Kingdom | 604/349 |

Primary Examiner—Randall L. Green
Assistant Examiner—Robert Clarke
Attorney, Agent, or Firm—David Pressman

[57] ABSTRACT

A male incontinence device comprises a condom (16) which fits over the end of a penis (17) and is secured by a band (11) having overlapping ends with H&L fasteners. When the condom is filled with a quantity of urine, it can be removed and emptied. Alternatively, the distal end of the condom has a valve (12, 13) thereat for manual emptying of the condom when it is in place. The valve may comprise a tubular housing (12) fitted into an end of the condom and a plug (3) which can be removably inserted into the housing. A brief-type undergarment (32) has a pouch 33 for supporting the condom when filled with urine (37). In lieu of a separate housing, the end of the condom may be thickened and formed into a tube (41) so that a plug (43) can be inserted into the tube. Alternatively, the end of the condom can be fitted with a ball-obturator valve (47, 49, 50) which can be opened to empty the condom by squeezing it from outside to distort the valve seat and thus open the seal formed by the ball obturator.

8 Claims, 3 Drawing Sheets

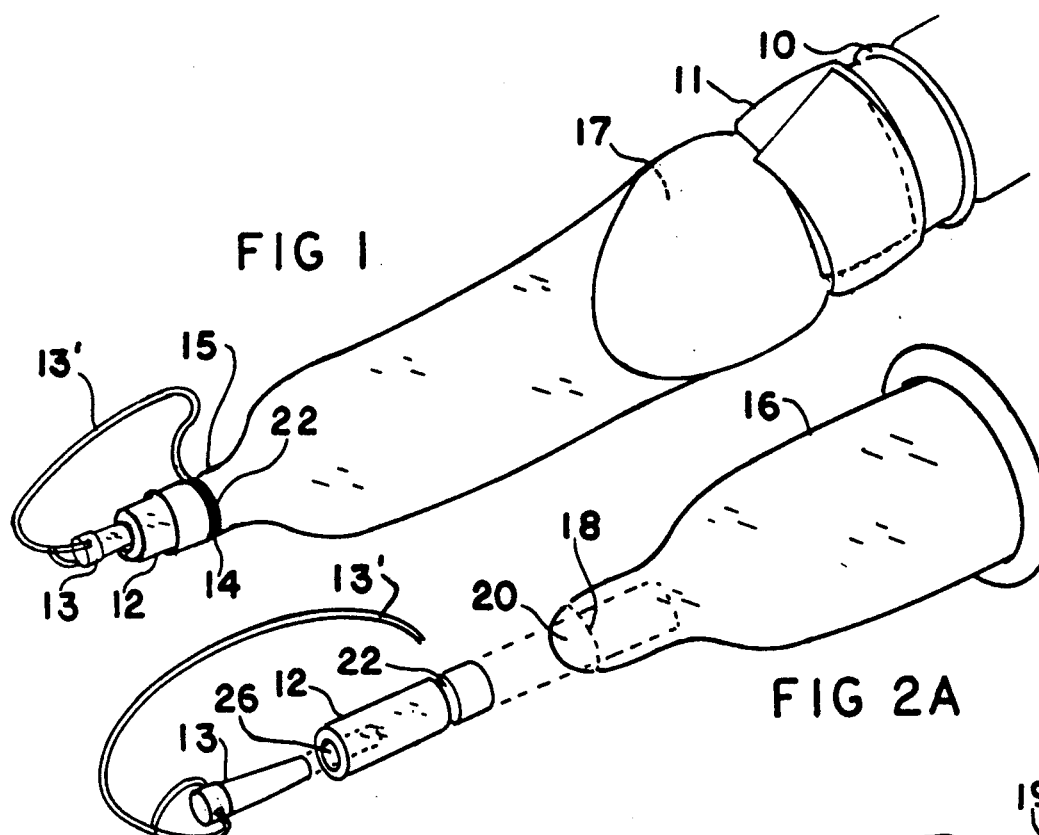
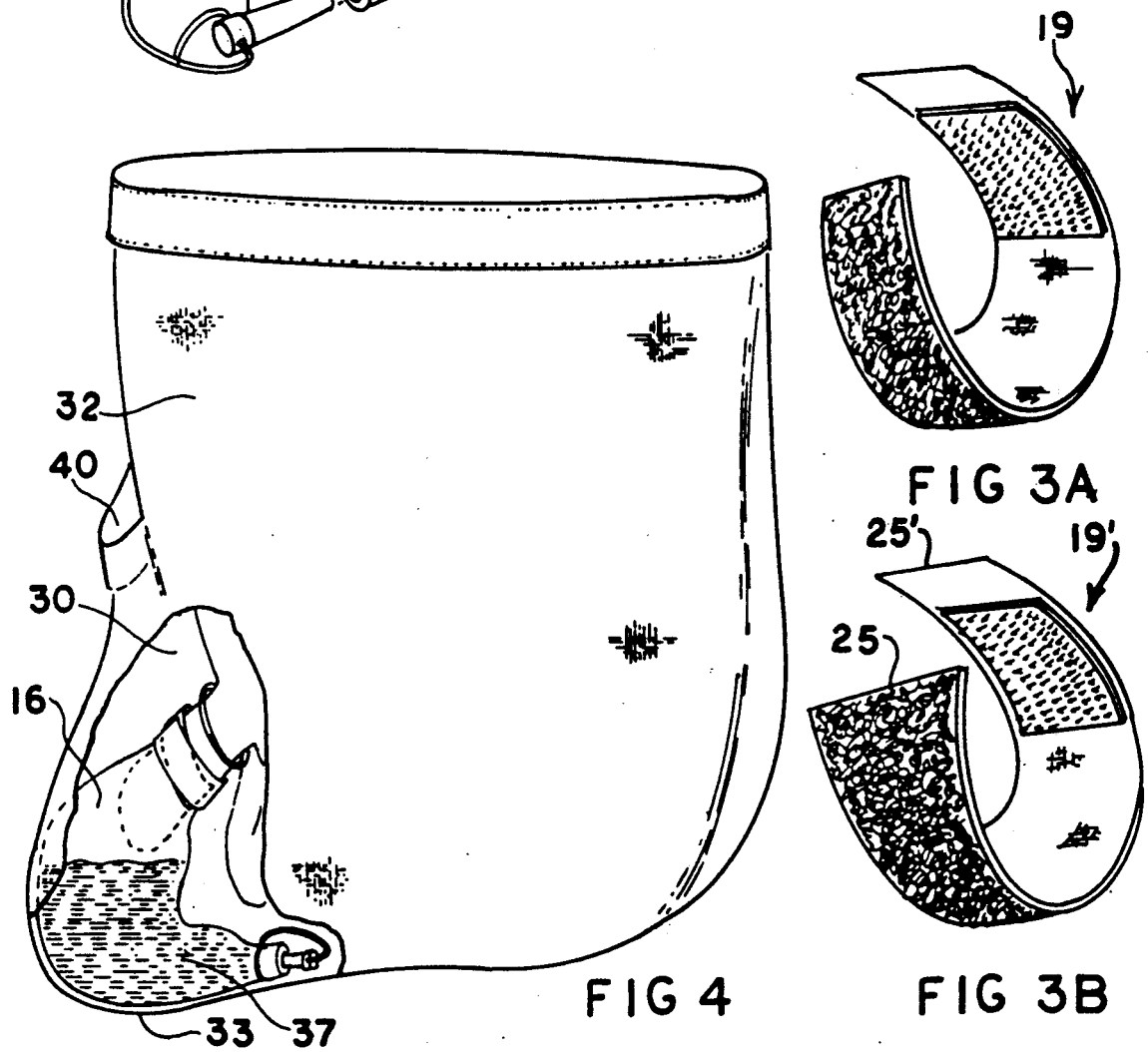

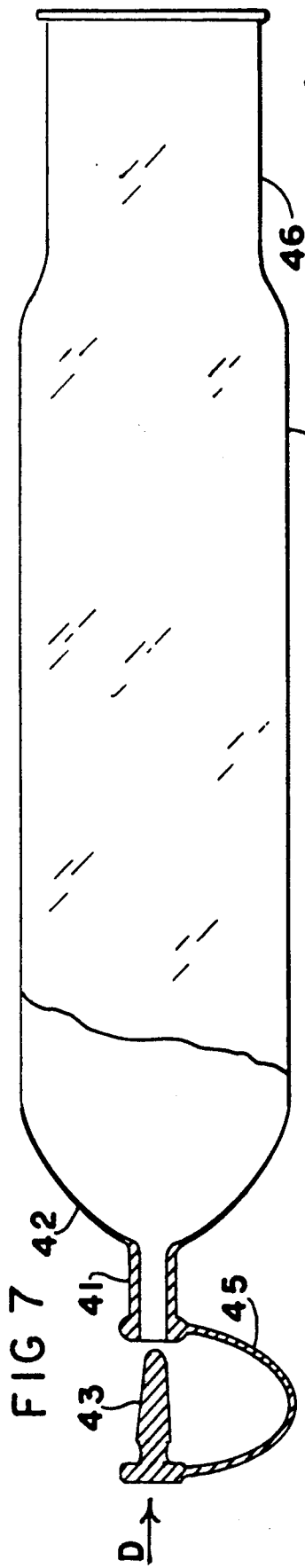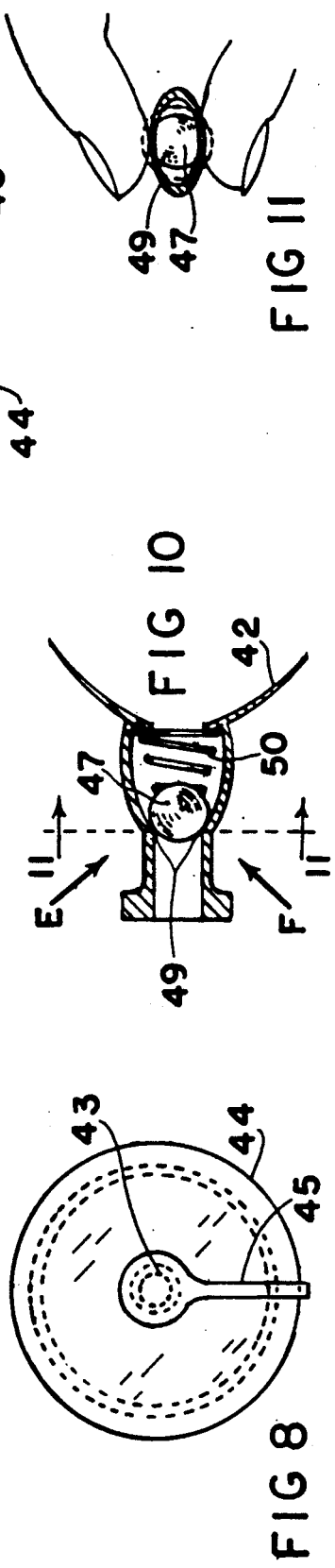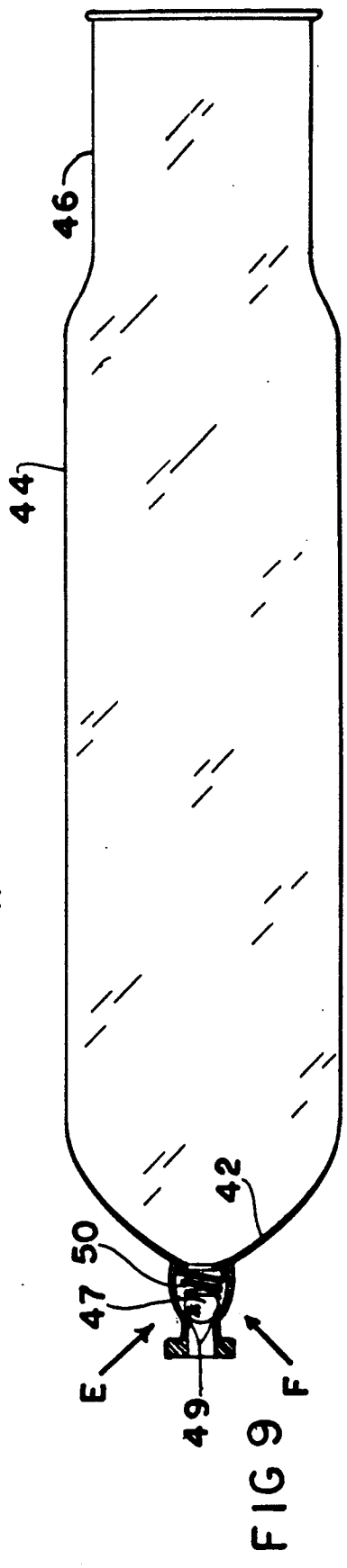

EXPANDABLE BANDED MALE URINARY INCONTINENCE CONDOM AND SUPPORTING UNDERGARMENT

BACKGROUND—FIELD OF INVENTION

The present invention relates to male urinary incontinence devices, in particular a urinary incontinence condom device and supporting undergarment.

BACKGROUND—DESCRIPTION OF PRIOR ART

In the past male urinary incontinence was primarily managed in two ways, internally and externally. Internal management was by means of a catheter, a tube introduced into the bladder through the urethra and which emptied into an external storage bag. This method resulted in irritation and discomfort, along with the danger of bladder infection, and could be used only for relatively brief periods.

External management was by means of condom devices. Since these are colloquially referred to by the medical profession as "external catheters" or "condom catheters," they will be referred to as such herein. These consisted of a sheath which was fitted over the penis, which was similar to a condom but thicker and heavier, so as to exert more elastic pressure. It was connected to a storage bag via a tube. Less conducive to infection than an internal catheter, the condom "catheter" was intended for use by men with long-term or chronic urine incontinence.

To say the least, the prior art male urinary condom device had many disadvantages. The storage bag was usually attached to the body, customarily to the leg or thigh, by two straps, and was connected to the condom portion by a plastic tube, the ends of which employed male-female pressure fittings to connect the tube to the condom portion and the storage bag, respectively. One problem was that, as urine collected in the storage bag, its weight increased, sometimes causing the connections to disengage or the condom to be pulled loose from the penis. Another disadvantage was that there were three sources of potential leakage, i.e., at both of its male-female connections and around the rim of the condom on the penis. The result was frequent spillage, soiling, and embarrassment to the wearer.

Another problem was that, in an attempt to secure the condom to the penis, strong adhesives often were used, causing the condom portion to stick too securely, in turn causing discomfort or damage to the skin while being removed. Another problem was caused by the elastic pressure exerted by the thick, heavy condom on the penis. This tended to reduce blood circulation and cause irritation and discomfort often amounting to pain. Another disadvantage was that the device was a bar to many normal activities, such as swimming, running, aerobics, horseback and motorcycle riding, and physical work.

Further problems related to the emptying of the bag of urine, as well with the attachment of the storage bag to the leg or thigh. Either the wearer had to undress in order to empty the bag, or he had to wear trousers loosely-fitting enough to allow him to roll up the trouser leg to get at it. Both methods were cumbersome and required him to take much longer to use a toilet or urinal than is normal. Moreover, if he had to drain the storage bag in a public urinal, he was faced with much embarrassment.

Another disadvantage was that there was no support for the storage bag beyond the straps fitted around the leg, which were both tight and uncomfortable yet insecure. I.e., the straps tended to restrict blood circulation yet could not always prevent the storage unit from slipping down the leg. Also, the storage bag prevented the user from wearing ordinary, closely-fitted street clothes, because the outline would show through, and also because the trouser leg could not be rolled up high enough to allow the user to get at it. The disabled had particular difficulty in handling such storage bags.

Another disadvantage was that, when going to bed, the wearer ordinarily had to detach the storage bag from his leg and attach it to the bedside or place it on the floor. This often prevented his free movement during sleep, as well as entailing the danger of disconnection and a resultant spill.

Another problem was that because the device was bulky, uncomfortable, and conspicuous under all but the baggiest clothing, it was embarrassing to the user. Still another problem was its costliness, due to the fact that the condom portion, and in some cases the storage bag as well, could only be used once.

The problems of the condom catheter were so great than some men were unable to cope with them. For such men, there was no alternative but to wear bulky and embarrassing adult diapers or to refuse to go out in public at all. For all these reasons, the urine-incontinent man was often severely handicapped in both his economic and social life.

OBJECTS AND ADVANTAGES

Accordingly, several objects and advantages of the present invention are to provide an improved device for controlling male incontinence, to provide an external "condom catheter" that consists of one unit only, without connecting tubes, to provide a means of collecting urine without the problems associated with weighing down, slippage, disconnections and leakage, to provide a device that is highly comfortable to the user, which does not restrict circulation to the penis sufficiently to cause irritation or impeded blood flow, and which can also be fitted and removed without pulling the skin or other difficulty. Further objects are to provide effective means for preventing a condom catheter from coming loose or coming off unintentionally, while at the same time presenting no problem when the user wishes to remove it. Another object and advantage is to permit the user to feel normal and confident during social activities, such as working, swimming, driving, running, skiing, dancing, or riding horses or motorcycles.

Still other objects and advantages are to provide simple means of storing and draining the urine without having to remove and replace the unit, and to provide storage for up to a pint of urine inconspicuously while the user wears normally styled and sized street clothing, or even exercise wear or swimming trunks. A further object is to allow the user to use a toilet or public urinal to drain his urine, in less time than it normally takes to empty a normal male bladder, without his engaging in any odd-looking and conspicuous activity, and without the need to undress or roll up his trousers.

Yet other objects are to accommodate and provide support for the condom by the use of a specially designed close-fitting undergarment brief, indistinguishable to the casual eye from other undergarments of its kind, to provide a device that is both easy-to-use for the elderly and disabled, while being compatible with the maximum freedom of movement for the otherwise healthy and active, to reduce expense to the user by providing a simple, low-cost unit that can be removed, easily washed, and used again, so that each unit can be used two or three times, and to provide an acceptable alternative to the bulky, odorous, and humiliating adult-sized diapers worn by urine-incontent men who have found themselves unable to cope with the previously existing condom devices.

BRIEF DESCRIPTION OF DRAWINGS

FIG. 1 is a perspective view of a condom catheter of the present invention.

FIG. 2 is a perspective view of the condom-like body of the device, together with a tube and plug valve part and connecting cord.

FIG. 3A is perspective view of a wrap-around band.

FIG. 3B is perspective view of a wide-end wrap around band.

FIG. 4 is a part perspective part sectional view of the invention worn by a user.

FIG. 7 is a part sectional, part perspective view of the preferred embodiment of the present invention, with an integrally made plug-valve and housing.

FIG. 8 is an end view of FIG. 7, taken in the direction of arrow D.

FIG. 9 is a part sectional, part perspective view of a condom catheter of FIG. 7, in which a spring-loaded obturator is used.

FIG. 10 is an enlarged view of the obturator of FIG. 9.

FIG. 11 is a sectional view of broken-line 11—11 of FIG. 10.

Reference Numerals

Figure 5:
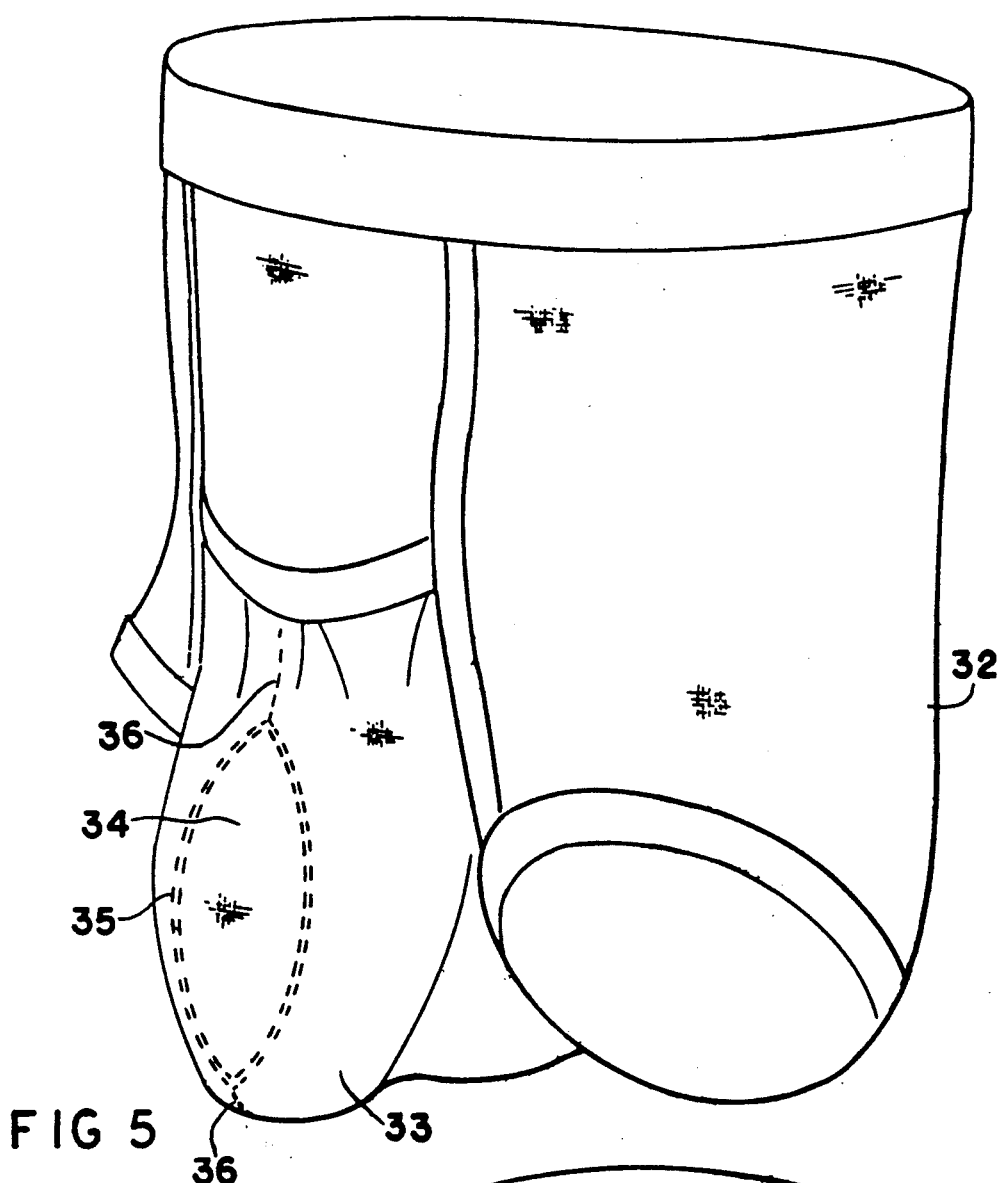
FIG. 5 is a perspective view of undergarment used in conjunction with the present invention.

10: large opening
11: wrap-around band
12: valve housing
13: plug valve
13': plug valve cord
14: thread
15: neck
16: condom
17: head
18: broken line
19: band with hook-and-loop fastener
19': modified band
20: semen reservoir
22: annular groove
25: wide loop end
25': hook end
26: valve end
30: cut away portion
32: undergarment brief
33: pouch
34: gusset
35: broken line
36: seam
37: urine
40: opening
41: valve housing
42: thickened end
43: valve
44: production unit condom
45: strap
46: open end
47: obturator
49: seat
50: spring

DETAILED DESCRIPTION

FIG. 1 show a urinary catheter or device 16 according to the invention. It has a large opening or rim 10 at its proximal (right) end and a wrap-around band 11 with multiple hook-and-loop fasteners adjacent the proximal end. A modified wrap-around band 19' (FIG. 3B) has a wide loop end 25 which provides extra width for the fingers to hold while hook end 25' is being attached. At the other end, the condom tapers to a neck 15. Positioned in neck 15 is a valve housing 12 with a plug valve 13 inserted into housing 12. A binding thread 14 secures valve housing 12 to neck 15 to form a leak-proof seal. A plug valve cord 13' is attached to plug valve 13 and valve housing 12.

FIG. 2 shows condom 16 in a partly unrolled condition. Its semen reservoir tip 20 is partially removed by cutting along broken line 18. Valve housing 12 preferably is made of rubber or vinyl and incorporates an annular groove 22 which is inserted into neck 15 about 1.3 cm (½ in). About 15 to 20 cm (6 to 8 in) of fine thread 14 is then wrapped tightly around annular groove 22 over neck 15 to force it into the groove to form a seal. Removable plug 13 is then inserted into open valve end 26. In addition, a cord 13' is attached to plug 13 at one end and to valve housing 12 at its other end. This insures that plug 13 cannot be accidentally dropped or lost when it is removed during use.

FIG. 3A shows wrap-around band 19 which is placed between rim 10 of condom device 16 (FIG. 1) and the head 17 of the penis to secure the catheter in place. Band 19 has multiple hook-and-loop fasteners sold under the trademarks VELCRO and LATCHLOCK.

FIG. 3B shows a wrap-around band 19' made wider at end 25, so as to provide extra width to hold while pulling and attaching narrow end 25'. This assists the user in fitting it tightly enough to form a leak-proof seal and also in preventing the condom from slipping off the penis.

FIG. 4 shows a specially modified brief or undergarment 32. A cut away portion 30 of brief 32 exposes condom 16 as worn by a user. During use, condom 16 will be expanded by urine 37. Brief 32 has a pouch 33 to house and support the expanded condom. Brief 32 also has an opening 40 above pouch 33. In use, to drain the catheter of urine, the user need only lift the catheter out of the pouch through opening 40 and withdraw valve plug 13, while directing the released urine into a urinal or toilet.

Figure 6:
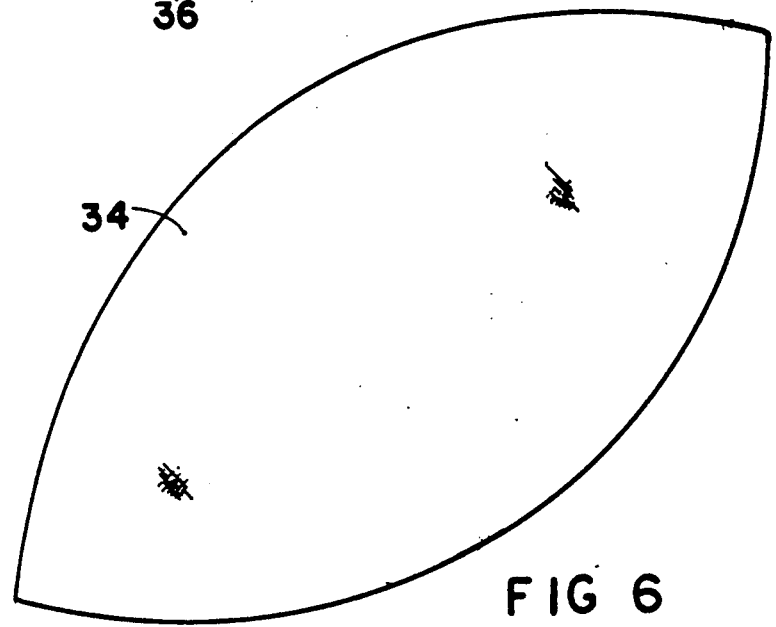
FIG. 6 is a gusset for sewing into the undergarment.

Undergarment—FIGS. 5 and 6

FIG. 5 details undergarment brief 32. It was made by modifying close-fitting commercial briefs, such as those sold under the trademark KANGAROO. Its pouch 33 has been formed by sewing in a gusset 34 (FIG. 6) which is made of similar material to the rest of the brief. FIG. 5 shows how gusset 34 has been sewn into the brief along double broken line 35 after seam 36 has been partly undone. Gusset 34 thereby enlarges the area of the brief so as to form pouch 33 and make it large enough to accommodate enlarged condom 16 (FIG. 4) even when expanded by as much as a pint of urine.

However, as the user will become aware of the growing bulk of the condom and pouch, he will ordinarily will take the opportunity to empty it of urine before it becomes as heavily filled as is illustrated.

Production Units—FIGS. 7 and 8

The present invention has been made from large-sized commercial condoms, which have proven perfectly satisfactory over 18 months of daily testing. During this time the user has engaged in heavy, full-time physical labor, traveled extensively by a 4-wheel drive vehicle through rough country, and also enjoyed dancing, swimming, and sports while wearing such condom catheters exclusively and continuously. Nevertheless, it is preferred that production condoms be made of slightly thicker material and be made about 20 cm (8 in) long. Also, the distal end of condom 44 should be made even thicker—1 mm (1/32 in) as illustrated at 42 in FIG. 7.

Production units can be made of rubber, latex, or any suitable material. Additionally, it is preferred that a valve 43 (FIG. 7 and 8) and valve housing 41 of the plug type be integrally made with thickened end 42 of condom 44. Valve housing 41 is connected to plug 43 by a strap 45. Condom 44 is 4.5 mm (1¾ in) in diameter and has a reduced diameter open end 46 of 3.5 mm (1⅜ in) diameter for a distance of about 4 to 5 cm (1½ to 2 in). When draining accumulated urine from condom 44, plug 43 is removed with one hand while holding valve housing 41 with the other.

FIGS. 9, 10 and 11

FIGS. 9 and 10 shows an alternative valve, in which a ball obturator 47 is pressed against a seat 49 by a spring 50. The user can operate this valve to release the urine by simply applying pressure with his forefinger and thumb in the direction of arrows E and F. This will cause obturator 47 to move away from seat 49 while at the same time elongating seat 49, as shown clearly in the cross-sectional view (FIG. 11). This distortion of a round seat to an oval seat allows fluid to bypass obturator 47. When finger and thumb pressure is released, the seat will return to round and spring 50 will return obturator 47 to its seat 49, thus re-effecting a water-tight seal.

One advantage of this valve is that it takes only one hand to operate the valve and drain the accumulated urine and replace the catheter into the pouch of the undergarment. This is a perfectly natural action by any person using a urinal and would not ordinarily be noticed by another person.

Description of Operation

In operation, the user unrolls or slips the condom over his penis into position as illustrated in FIG. 1. Ordinarily, this does not present a problem. Should a lubricant be required, water can be used. However, moisture tends to allow the condom to slip down the penis. This can be prevented by first applying a very thin film of denture adhesive cream around the upper part of the shaft of the penis before completing the unrolling of the condom. Unlike the adhesives used generally in condom urinary devices, dental adhesive cream prevents slipping, without adhering like glue to the skin and without causing discomfort. It also washes off easily with water.

Once the condom is in place, the band is applied. The user places the loop end of the band just below the rim of the condom. He holds that end in place while simultaneously pulling the band snugly around the circumference of the penis. Then he presses the hook end over the loop end, so that the hooks and loops mesh. The band should be tight enough to hold the condom firmly in place without exerting an uncomfortably degree of pressure on the penis. The user's briefs are then drawn on the condom is guided into the enlarged pouch of the briefs.

As urine accummulates, the condom will expand. The pouch will hold the condom and its contents comfortably and securely until it is convenient for the user to empty it. At that time, the user will ease the urine-filled catheter out through the opening in the pouch, open the valve, and aim the stream of urine into a urinal or toilet. When the urine has drained, he will close the valve and slip the condom back into the pouch.

At least once a day, the user should remove the condom device, wash it in warm, soapy water, then rinse and dry it thoroughly before putting it back on. After two or three such washings, the condom should be discarded and replaced, as it will tend to weaken. Ideally, for those who can afford it, a fresh condom device will be used each day.

Summary, Ramifications, and Scope

Thus, the reader will see that the present invention has many advantages over prior-art male incontence device, i.e. the user enjoys normal and natural freedom, normal social activities, such as working, swimming, aerobics, driving, running, skiing, dancing, or riding horses or motorcycles. He enjoys freedom from feeling the weight of accumulated urine on his leg, from tacky adhesives, from the pain of excessive pressures, and from the dragging down of leg straps. He can dress in everyday street clothing, and his incontinence is completely inconspicious to all, even when standing side by side with other men at a public urinal. Furthermore, he can drain the condom just as fast or faster than others can empty their bladders.

Not only is the condom easy to fit and secure, but it is also very convenient, simple to pack in quantity, takes up little room, is not bulky or heavy, nor is it costly. It is also not malordorous. Used condoms can be disposed of like toilet paper, so that no bulky parcels in plastic bags and wrappers are left for disposal. The user can even enjoy long periods of driving with no urgency to get to a toilet when none is available. Although most men will empty the condom when it contains no more than about ¼ liter, the condom under test can hold at least a gallon. Although the increase in bulk will alert the user to empty it in a timely manner, there is no sensation of weight. Finally, the ease of use makes it highly advantageous for the elderly or partially disabled, in that it is easy to use, does not require rolling up one's pants leg, and so spares them much embarrassment.

While the above description contains many specificities, the reader should not construe these as limitations on the scope of the invention, but merely as exemplifications of preferred embodiments thereof. Those skilled in the art will envision that many other possible variations are within its scope. For example, other forms of attaching the condom, such as with a tie band, an elastic band, or adhesive could be used. The attachment means should alone be sufficient to retain the condom when it contains about 100 grams of urine. The condom can be relatively short, covering just the distal end of the penis, or it can be made of relatively thicker, more expandable rubber in its proximal and middle portions, so that only its distal end can expand. The distal end portion should be able to expand enough to hold at least 100 grams of urine.

It would also be possible to use an ordinary commercial condom, securing it by any of the above means, and simply removing and replacing it each time it became filled. Also, the condom could be made longer, shorter, or bigger, or be fitted with any suitable valve, such as a rotary thumb-screw valve, a pressure screw-type valve, or a clamp pressure-type valve. Also, the user could wear a regular, unmodified brief undergarment and a suitable athletic supporter or other dedicated pouch, separate from the user's ungarment, and supported by its own attaching waist band in place of the modified brief.

Accordingly, the reader is requested to determine the scope of the invention by the appended claims and their legal equivalents, and not by the examples which have been given.

We claim:

1. A method for enabling a urine-incontinent male to carry voided urine conveniently until he can dispose of same, comprising:
   fitting a condom having a closed distal end and an open proximal end over at least the distal end of the penis of a wearer, at least the distal end portion of said condom being sufficiently flexible, stretchable, and expandable that when said condom is fitted over said penis and affixed to said penis above said distal end portion of said penis and urine is introduced between said closed distal end portion of said condom and the distal end of said penis, said urine will force said closed distal end portion of said condom to stretch and expand to a larger diameter and away from said distal end of said penis so as to be able to retain at least 100 grams of urine in said closed distal end portion of said condom,
   securing said condom to said penis above said distal end of said penis so that said condom will remain on said penis even when said urine fills and forces said distal end portion to stretch and expand, and said condom has no support other than said securing means, and
   providing an undergarment containing a pouch in a symmetrical location with respect to said wearer's legs for supporting said condom when it is filled with urine.

2. A male incontience device for enabling a urine-incontinent male to carry voided urine conveniently until he can dispose of same, comprising:
   a condom having a closed distal end and an open proximal end and being sized so that it can be fitted over at least the distal end of the penis of a wearer,
   at least the distal end portion of said condom being sufficiently flexible, stretchable, and expandable that when said condom is fitted over said penis and urine is introduced between said distal end portion and the distal end of said penis, said distal end portion of said condom will stretch and expand to a larger diameter and away from said distal end of said penis so as to be able to retain at least 100 grams of urine,
   securing means for securing said condom to said penis above said distal end thereof so that said condom will remain on said penis of said wearer even when said distal end portion is filled with said 100 grams of urine and said condom has no support other than said securing means, and
   an undergarment, said undergarment containing a pouch in a symmetrical location with respect to said wearer's legs for supporting said condom when it is filled with urine.

3. The male incontinence device of claim 2 wherein said securing means comprises an elongated band having two end portions, said band being long enough to be wrapped around said condom when said condom is fitted over said penis such that said end portions thereof overlap, said end portions containing means for securing said end portions together in an overlapping relationship.

4. The male incontinence device of claim 2 wherein said distal end of said condom has an opening, and further including a tubular plug valve housing inserted into said opening, means for hermetically sealing said housing to the portion of said condom adjacent said opening, and a plug valve member removably installed in said housing, whereby said plug valve member can be removed to empty urine accumulated in said condom, and reinserted in said housing to re-seal said condom for subsequent accumulation of urine.

5. The male incontinence device of claim 2 wherein said closed distal end of said condom has an opening, the portion of said condom adjacent said opening being tubularly shaped and being thicker and more rigid than the rest of said condom so that said opening is at the end of said tubular section of said condom, and further including a plug valve member removably inserted into said opening, whereby said plug valve member can be removed to empty urine accumulated in said condom, and reinserted in said opening to re-seal said condom for subsequent accumulation of urine.

6. A male incontinence device for enabling a urine-incontinent male to carry voided urine until he can dispose of same, comprising:
   a condom having a closed distal end and an open proximal end and being sized so that it can be at least partially fitted over the distal end of the penis of a wearer,
   securing means for securing said condom to said penis above said distal end thereof so that said condom will remain on said penis of a wearer thereof even when said proximal end thereof contains a quantity of urine and said condom has no support other than said securing means,
   said distal end of said condom being made sufficiently flexible, stretchable, and expandable that when said condom is fitted over said penis and urine is introduced between said distal end portion, said distal end portion of said condom will stretch and expand to a larger diameter and away from said distal end of said penis so as to be able to retain at least 100 grams of urine, and
   releasing valve means at said closed distal end of said condom for selectively releasing urine accumulated in said condom without removing said condom from said penis, and
   an undergarment, said undergarment containing a pouch in a symmetrical location with respect to said wearer's legs for supporting said condom when it is filled with urine.

7. The male incontinence device of claim 6 wherein said releasing means comprises a valve seat and a ball obturator, and further including means for continually urging said ball obturator against said seat, said valve having a cylindrical body which is flexible enough to be deformed so that when said body is deformed, said seat will be distorted so as to break the seal of said ball obturator against said seat.

8. The male incontinence device of claim 6 wherein said releasing valve means at said closed distal end of said condom comprises an opening in said distal end of said condom, the portion of said condom adjacent said opening being tubularly shaped, thicker, and more rigid than the rest of said condom, and further including a plug valve member removably inserted into said opening, whereby said plug valve member can be removed to empty urine accumulated in said condom, and reinserted in said opening to re-seal said condom for subsequent accumulation of urine.

* * * * *